(12) United States Patent  (10) Patent No.: US 7,308,311 B2
Sorensen et al.  (45) Date of Patent: Dec. 11, 2007

(54) PHYSICIAN PROGRAMMER SYSTEM WITH TELEMETERED SENSOR WAVEFORM

(75) Inventors: Chris Sorensen, Valencia, CA (US); Euljoon Park, Valencia, CA (US); Jorgen Edvinsson, Gustavsberg (SE)

(73) Assignee: Pacesetter, Inc., Sylmar, CA (US)

( * ) Notice: Subject to any disclaimer, the term of this patent is extended or adjusted under 35 U.S.C. 154(b) by 626 days.

(21) Appl. No.: 10/302,348

(22) Filed: Nov. 22, 2002

(65) Prior Publication Data

US 2004/0102814 A1    May 27, 2004

(51) Int. Cl.
*A61N 1/00* (2006.01)
*A61N 5/04* (2006.01)
*A61N 5/00* (2006.01)

(52) U.S. Cl. .................. 607/32; 600/301; 600/523; 607/17

(58) Field of Classification Search ................ 600/523, 600/300, 509, 301; 607/32, 60, 17
See application file for complete search history.

(56) References Cited

U.S. PATENT DOCUMENTS

| 4,702,253 | A | 10/1987 | Nappholz et al. ..... 128/419 PG |
| 4,901,725 | A | 2/1990 | Nappholz et al. ..... 128/419 PG |
| 6,347,245 | B1 * | 2/2002 | Lee et al. .................... 600/523 |
| 6,472,991 | B1 * | 10/2002 | Schulman et al. ....... 340/995.1 |
| 6,694,179 | B1 * | 2/2004 | Mouchawar et al. ........ 600/523 |
| 6,748,274 | B2 * | 6/2004 | Levine et al. ................. 607/32 |
| 2002/0123770 | A1 | 9/2002 | Combs et al. ................. 607/9 |

FOREIGN PATENT DOCUMENTS

| WO | WO 98/14772 | 4/1998 |
| WO | WO 02/051497 A2 | 7/2002 |

* cited by examiner

*Primary Examiner*—Mark Bockelman

(57) ABSTRACT

A programmer and implantable stimulation device system with the implantable device and programmer in telemetric communication with each other wherein the implantable device internally monitors a plurality of physiological parameters and telemeters a plurality of those parameters to the programmer in at least a quasi-real-time manner such that the programmer can display waveforms corresponding to the internally monitored parameters in at least a quasi-real-time manner. The physiological parameters can include measurements of cardiac function, metabolic need, and patient orientation. In some aspects, the internally monitored parameters are provided continuously in a real-time manner and, in other aspects, the parameters are processed to a limited extent and provided as a derived parameter, such as an average, and/or as frames of data.

21 Claims, 7 Drawing Sheets

PHYSICIAN PROGRAMMER SYSTEM WITH TELEMETERED SENSOR WAVEFORM

FIELD OF THE INVENTION

The invention relates to a physician programmer for implantable medical devices that telemeter sensor signals to a programmer for display on the programmer in concert with a telemetered IEGM signal and Markers.

BACKGROUND OF THE INVENTION

Implantable cardiac devices provide patients with automatic monitoring of cardiac activity and delivery of programmed therapy upon detection of certain cardiac arrhythmia's. The initial and ongoing clinical care provided to patients with implantable cardiac device systems often includes the use of programmers. Implantable cardiac devices are typically provided with telemetry circuits and programmers are devices that enable a clinician to telemetrically communicate with and control an implantable cardiac device, such as a pacemaker or defibrillator.

Implantable devices often monitor and record a variety of internal physiological parameters of the patient as well as data relating to device operation and status and periodically telemetrically transmit this measured and recorded information outside the patient's body to a programmer. Programmers are generally provided with displays to allow a clinician to review the data via the programmer and make any indicated changes in the patient's therapy.

One common type of internally monitored information telemetrically provided by an implantable device for display on a programmer is provided as waveforms derived from electrical cardiac signals obtained internally, typically via leads directly on or within cardiac tissue, and variously referred to as intracardiac electrograms (IEGM) or electrograms, egrams, or EGMs. The IEGM waveform indicates internally measured propagation of low amplitude electrical signals, commonly referred to as the cardiac impulse, across the myocardium giving information about depolarization and repolarization characteristics of the heart.

The ongoing clinical care provided to patients with implantable cardiac device systems also often includes the use of surface electrocardiograms (ECG). The ECG also provides information regarding propagation of the cardiac impulse, however, as measured on the skin surface of the patient. A surface ECG is a highly useful diagnostic aid for clinicians for the study of heart rate and rhythm and to confirm proper operation of the implantable device's sensing function via comparison with the device generated IEGM signal.

An ECG is typically obtained from signals from a plurality of electrodes (3, 5, and 12 are common numbers) that are placed on the patient's skin surface. The ECG indicates monitored voltage signals appearing between various pairs of the electrodes and reflects a vector analysis of the resultant signal pairs to prepare various two-dimensional voltage-time graphs indicative of internal cardiac activity. Again, surface ECG refers to placement of electrodes on the surface, or skin, of the patient as opposed to directly to cardiac tissue as in an IEGM.

Additional implantable sensors are known and can provide additional information to an implantable cardiac stimulation device relating to metabolic need, patient activity level, patient orientation, etc. to further refine the delivery of appropriate therapy. For example, $O_2$ saturation sensors can provide information relating to metabolic utilization of blood oxygen that can indicate a change in pacing rate. 3-D accelerometers can provide information relating to both patient orientation (supine, standing, etc.) as well as activity level (still, walking, running, etc.) that can also indicate a change in therapy delivery. Sensors are also available that can provide quantitative information on respiration rate and depth also indicative of metabolic need.

Current telemetry typically operates at 8k and can accommodate up to two channels of IEGM data, along with one frame of event markers. Markers are real-time annotations of paced and sensed events and can be graphically displayed concurrent with a surface electrocardiogram (ECG) waveform and/or an IEGM waveform via the display of a programmer. The IEGM data is generally composed of four frames of data. The two channels can be sampled at 256 bytes/second, with each channel using two frames. Alternatively, a single IEGM channel can be sampled at 512 bytes/second using all four frames for the single channel.

It is desirable to be able to provide a clinician with as much and as detailed information as possible, however, it will be understood that bandwidth limitations limit the amount/rate at which data can be transferred. In particular, an 8k telemetry system is typically limited to providing only the IEGM and marker information identified above with data related to device performance/operation. Thus, other sensor data that may be available to the implantable device is typically not available on a real-time basis to the clinician.

Real-time data is preferred as it provides useful detail that can be lost in a derived value, such as a total count or average value. Real-time data also enables a clinician to compare internally monitored data with direct observation of the patient and/or other data such as from surface monitoring. However, in certain applications, it can be desirable to have a quasi-real-time presentation of data to enable processing of raw data so as to obtain, for example, marker data, a rate, or an average value or to present waveforms in frames. With available processing means, this level of processing can generally provide information that on the scale of human perception is indistinguishable from true real-time presentation.

It will be understood that telemetry rate is generally dependent on available power. Implantable devices are typically battery powered and increasing telemetry rate typically increases power drawn from the battery thereby reducing battery life, often to an undesirable degree. Replacement of a depleted battery typically requires an invasive explantation procedure and is thus desirably extended as long as possible. In addition, for many currently used technologies, the battery directly powers the device (typically referred to as an unregulated device). Increasing the power drawn from the device reduces the available battery voltage which can impair device operation.

From the foregoing, it can be understood that there is an ongoing need for an implantable device programmer system that can provide a clinician with additional diagnostic information of multiple internally monitored physiological parameters on a real-time basis.

SUMMARY

In one embodiment, a system is provided for telemetering sensor data as it is provided to the device bus and formatting the data for transmission and display on a programmer. The telemetered sensor data can then be graphically displayed for use by a physician or researcher. The sensor data can also be stored for later off-line review by users. Particular embodiments of the sensor data graphically displayed include a scrolling impedance wave showing respiration in relation to the cardiac cycles, a hemodynamic sensor signal indicating pressure and/or volume changes with respect to the cardiac and respiration cycles, and a positional display showing the interpretation of the patient's position as indicated by a 3-D positional sensor.

In another illustrative embodiment, an implantable medical device is capable of internally monitoring parameters indicative of cardiac function, and includes at least one implantable sensor capable of monitoring at least one parameter indicative of patient status, and a telemetry circuit in communication with the implantable cardiac stimulation device and at least one implantable sensor wherein the telemetry circuit provides data corresponding to both the internally monitored parameters indicative of cardiac function and patient status in at least a quasi-real-time manner.

Yet another aspect of the invention is a method of providing correlated data from an implantable sensor and an implantable cardiac stimulation device for simultaneous viewing via a display device, the method comprising sensing at least one parameter with the implantable cardiac stimulation device, sensing at least one parameter with the implantable sensor, telemetrically transmitting at least one parameter sensed by each of the implantable cardiac stimulation device and the implantable sensor in at least quasi-real-time, and displaying at least one parameter from each of the implantable device and the sensor via the display device in a correlated manner.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Figure 1:
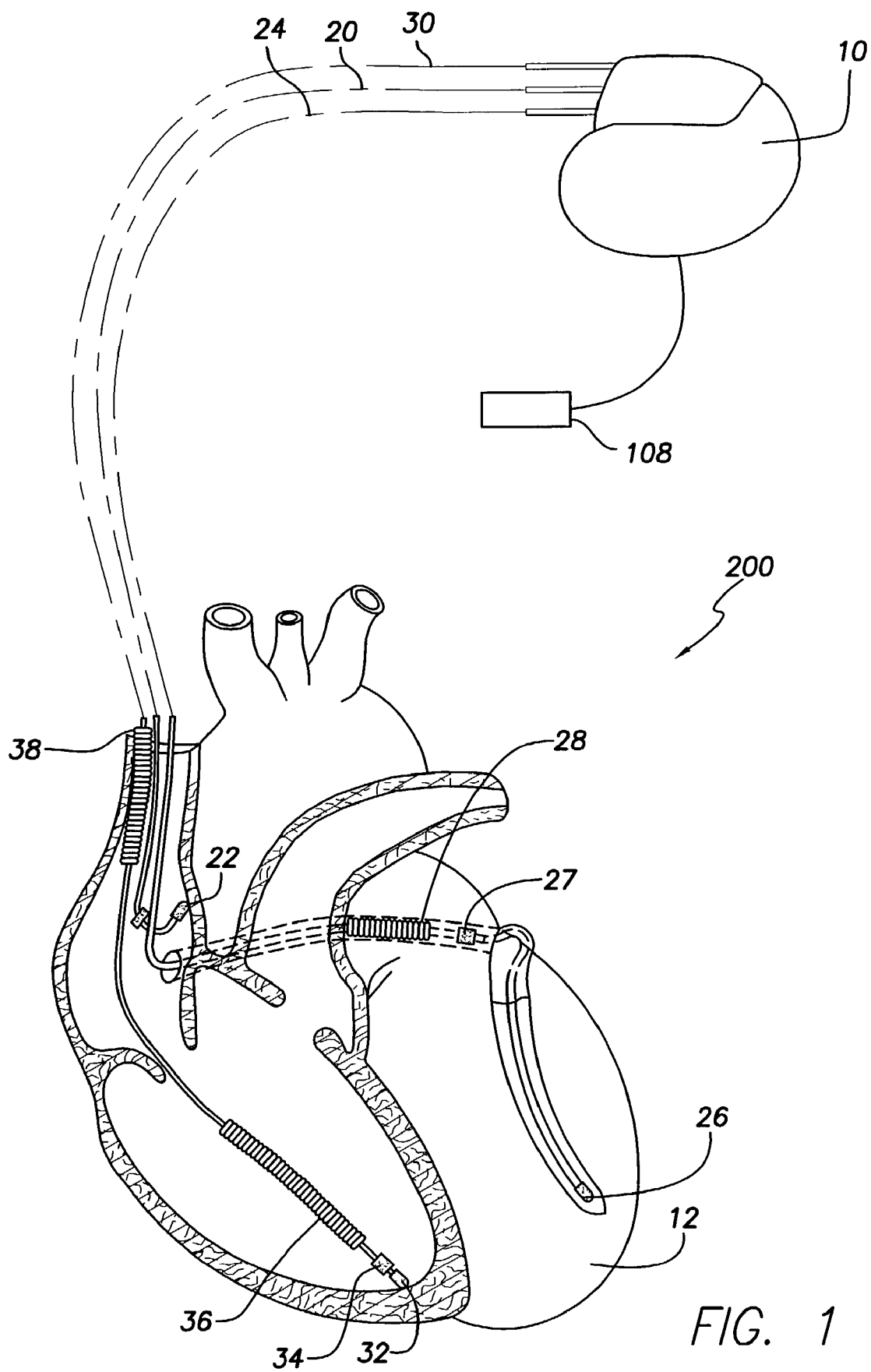
FIG. 1 is a diagram of an implantable cardiac device of a Physician Programmer System with Telemetered Sensor Waveform in communication with a patient's heart.

As shown in FIG. 1, there is one embodiment of a stimulation device 10 of a physician programmer system with telemetered sensor waveform 200 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber pacing therapy, the stimulation device 10 is coupled to a "coronary sinus" lead 24 designed for placement in the "coronary sinus region" via the coronary sinus ostium (OS) for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular pacing therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

FIG. 1 also shows at least one implantable sensor 108 in communication with the device 10. The at least one sensor 108 internally monitors parameters of clinical interest relating to patient condition or status. In various embodiments of the invention, the sensor 108 can provide information relating to respiration rate and/or tidal volume, arterial and/or venous $O_2$ saturation, heart stroke volume, temperature, patient orientation and/or movement, and hemodynamic status such as pressure. FIG. 1 illustrates the sensor 108 as being located outside the device 10, however, it will be understood that in alternative embodiments the sensor 108 can be co-located with the device 10 or contained therein. The exact placement or location of at least one sensor 108 can vary in different embodiments without detracting from the scope of the invention. It will also be understood that the communication between the sensor 108 and the device 10 can include wired or wireless communication in various embodiments.

Figure 2:
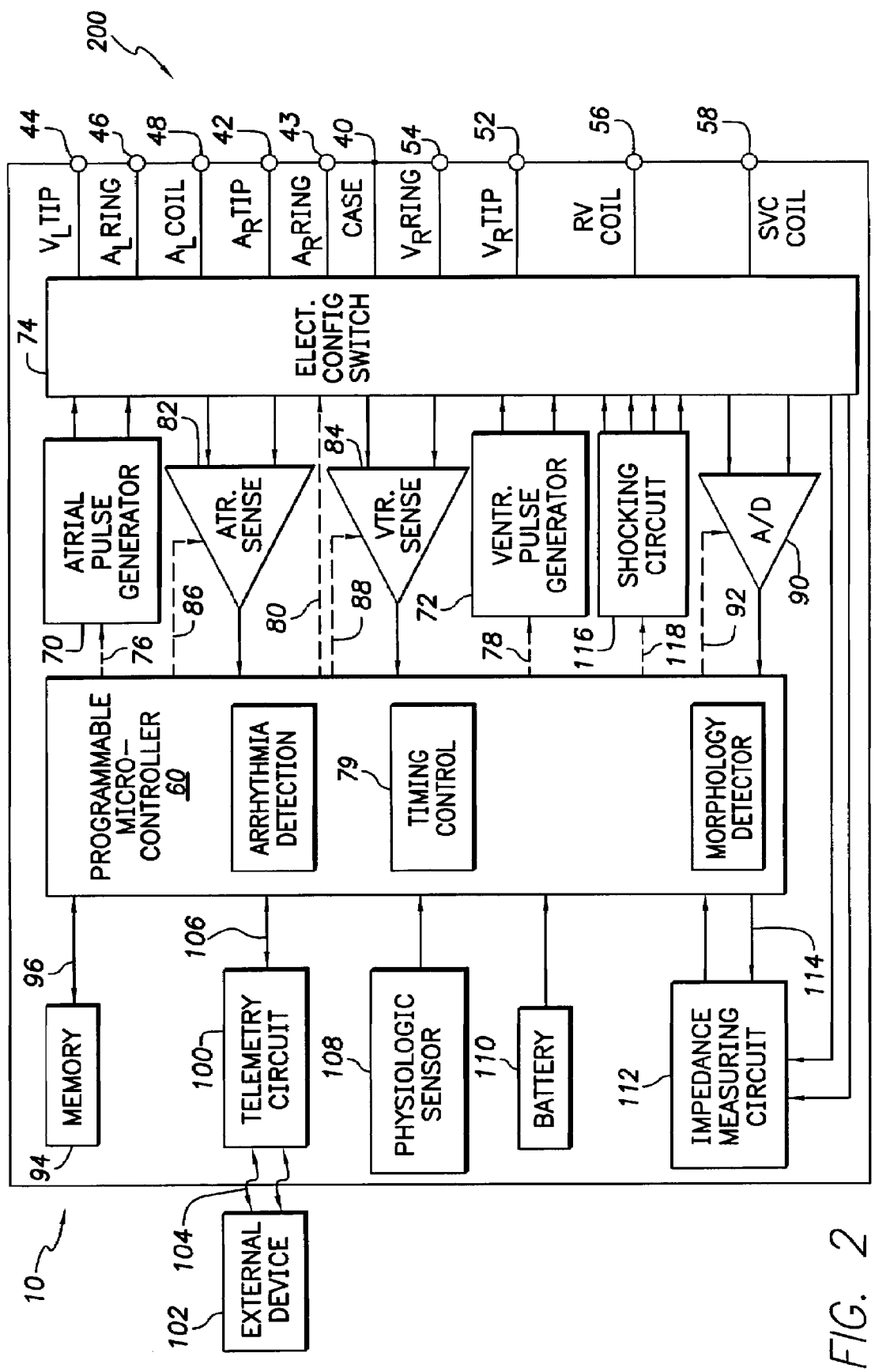
FIG. 2 is a functional block diagram of one embodiment of an implantable cardiac stimulation device and sensor of a Physician Programmer System with Telemetered Sensor Waveform.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

A housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The housing 40 further includes a connector (not shown) having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. As is well known in the art, the microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart 12, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc., which is well known in the art.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, combipolar, etc.) by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches, as is also known in the art. In this way, the clinician may program the sensing polarity independent of the stimulation polarity.

Each sensing circuit, 82 and 84, preferably employs one or more low power, precision amplifiers with programmable gain and/or automatic gain control, bandpass filtering, and a threshold detection circuit, as known in the art, to selectively sense the cardiac signal of interest. The automatic gain control enables the device 10 to deal effectively with the difficult problem of sensing the low amplitude signal characteristics of atrial or ventricular fibrillation. The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart.

For arrhythmia detection, the device 10 utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Figure 3:
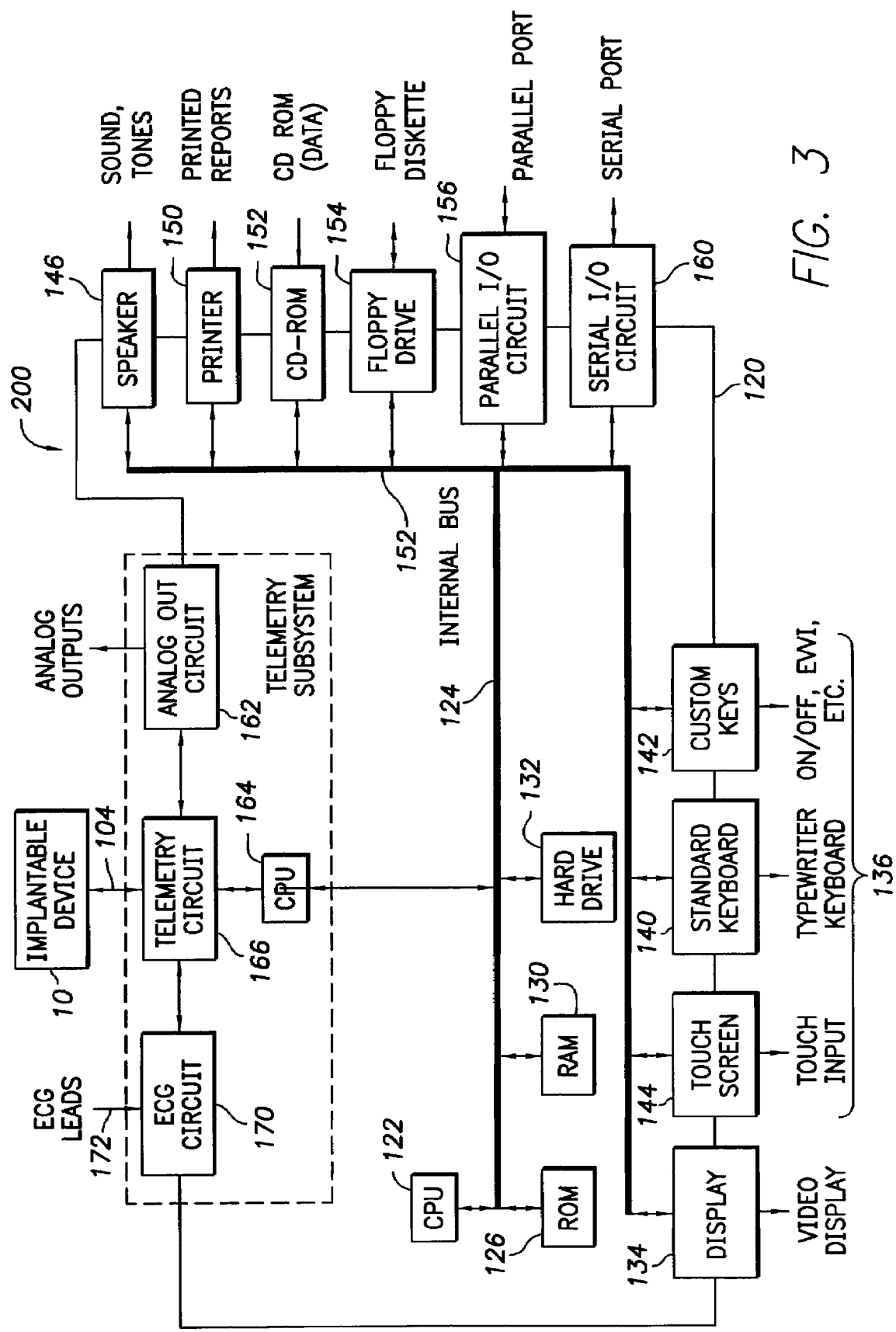
FIG. 3 is a functional block diagram of a programmer of a Physician Programmer System with Telemetered Sensor Waveform.

Cardiac signals are also applied to the inputs of an analog-to-digital (A/D) data acquisition system 90. The data acquisition system 90 is configured to acquire intracardiac electrogram (IEGM) signals, convert the raw analog data into a digital signal, and store the digital signals for later processing and/or telemetric transmission to an external device 102, which, in certain embodiments, comprises a programmer 120 (FIG. 3). The data acquisition system 90 is coupled to the right atrial lead 20, the coronary sinus lead 24, and the right ventricular lead 30 through the switch 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, desired operating parameters or other programming instructions of the implantable device 10 may be non-invasively programmed into the memory 94 through a telemetry circuit 100 in telemetric communication with the external device 102, such as a programmer 120 (FIG. 3), transtelephonic transceiver, or a diagnostic system analyzer. The telemetry circuit 100 may be activated from a standby condition in response to an indication from a radio frequency (RF) detector (not shown) that signals of a predetermined strength are being received. The telemetry circuit 100 can communicate with the microcontroller 60 via a communication link 106.

The telemetry circuit 100 also advantageously allows intracardiac electrograms and status information relating to the operation of the device 10 (as contained in the microcontroller 60 or memory 94) to be sent to the external device 102 through an established communication link 104 as well as data from the at least one sensor 108. In certain embodiments, data from the at least one sensor 108 is selectively sent continuously via the communication link 104 and, in alternative embodiments, the data from the sensor 108 is sent in frames and/or as a derived signal, e.g. an average or rate.

The telemetry circuit 100 may advantageously operate at increased transmission rates. Increased data transmission rates of the telemetry circuit 100 enables the device 10 to transmit more data and/or data of increased detail than other devices. This aspect facilitates the display of additional information via the programmer 120 in a manner that will be described in greater detail below.

The at least one physiologic sensor 108 is commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V-V Delay, etc.) at which the atrial and ventricular pulse generators, 70 and 72, generate stimulation pulses.

While shown in FIG. 2 as being included external to the stimulation device 10, it is to be understood that the physiologic sensor 108 may also be within the stimulation device 10 and may include a variety of sensors 108 some or all of which may be external to the device 10, yet still be implanted within or carried by the patient. A common type of rate responsive sensor is an activity sensor, such as an accelerometer or a piezoelectric crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc. It is also to be understood, that in certain embodiments, the sensor 108 is capable of sensing multiple parameters and providing all the sensed parameters or a selected number of the parameters to the device 10.

Examples of suitable sensors 108 that may be advantageously employed in various embodiments of the system 200 are described in U.S. Pat. Nos. 4,901,725 and 4,702,253A1 directed towards obtaining respiration signals, and WIPO publication WO 98/14772 A1 for "Electrochemical Sensor" describing a partial oxygen pressure sensor, all of which are incorporated herein by reference.

The stimulation device additionally includes a battery 110 which provides operating power to all of the circuits shown in FIG. 2. For the stimulation device 10, which employs shocking therapy, the battery 110 must be capable of operating at low current drains for long periods of time, and then be capable of providing high-current pulses (for capacitor charging) when the patient requires a shock pulse. The battery 110 must also have a predictable discharge characteristic so that elective replacement time can be detected.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used. The impedance measuring circuit 112 is not critical to the invention and is shown for only completeness.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5-10 joules), or high energy (11 to 40 joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5-40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

FIG. 3 is a functional block diagram of one embodiment of the programmer 120 illustrating greater details thereof. A CPU 122 is in communication with an internal bus 124. The internal bus 124 provides a common communication link and power supply between the various electrical devices of the programmer 120, including the CPU 122. The programmer 120 also comprises memory and storage including ROM 126, RAM 130, and a hard drive 132 in communication with the internal bus 124. The ROM 126, RAM 130, and hard drive 132 provide temporary memory and non-volatile storage of data in a well known manner. In particular, the ROM 126, RAM 130, and hard drive 132 can store programmed control programs and commands for upload to the implantable device 10 as well as control programs for display of data received from the implantable device 10 as is well understood in the art. It will be appreciated that, in certain embodiments, alternative data storage/memory devices, such as flash memory, can be included or replace at least one of the ROM 126, RAM 130, and hard drive 132 without detracting from the spirit of the invention.

The programmer 120 also comprises a display 134. The display 134 is adapted to visually present graphical and alphanumeric data in a manner well understood in the art. Specific examples of data presented via the display 134 in various embodiments will be described in greater detail below with reference to FIGS. 4-8.

In certain embodiments, the programmer 120 also comprises input devices 136 comprising, in this embodiment, a keyboard 140, a plurality of custom keys 142, and a touchscreen 144 aspect of the display 134. The keyboard 140 facilitates entry of alphanumeric data into the programmer system 100. The custom keys 142 are programmable in order to provide one touch functionality of predefined functions and/or operations of the system 100. The custom keys 142 may be embodied as dedicated touch keys and/or as predefined areas of the touchscreen 144.

In certain embodiments, the programmer 120 also comprises a speaker 146 and a printer 150 in communication with the internal bus 124. The speaker 146 is adapted to provide audible alerts and signals to a user and the printer 150 is adapted to provide a printed read-out of information as generated or monitored by the system 100.

The programmer 120 can also comprise a CD drive 152 and a floppy drive 154 which together provide removable storage of data. The CD drive 152 and the floppy drive 154 provide removable data storage and read capability for the programmer system 100 in a well understood manner.

In this embodiment, the programmer 120 also includes a parallel input-output (IO) circuit 156, a serial IO circuit 160, and an analog output circuit 162. These circuits 156, 160, 162 provide a variety of communication capability with other devices in a manner well understood in the art.

In this embodiment, the programmer 120 further includes a telemetry CPU 164 that is in communication with a telemetry circuit 166. The telemetry circuit 166 maintains the communication link 104 between the programmer 120 and the implantable device 10. As previously described, the communication link 104, in this embodiment, operates at an increased speed of 64 k. This aspect of the invention enables the programmer 120 and the implantable device 10 to exchange information at an increased speed to enable real-time transmission of signals obtained from the at least physiological sensor 108.

The programmer 120 also comprises an ECG circuit 170 in communication with a plurality of ECG leads 172. The ECG circuit 170 and the ECG leads 172 obtain electrical signals from the surface of a patient's body in a well understood manner and configure these signals for display as an ECG waveform 174 (FIG. 4) on the display 134 of the programmer 120.

It is to be understood that the components of the system 200 described above are exemplary and that additions or deletions of certain elements may be made without detracting from the spirit of the invention.

In various embodiments of the system 200, functions provided by at least one of the input devices 136 of the programmer 120 include selection of an electrocardiogram (ECG) and/or an intracardiac electrogram (IEGM) for display on the display 134. The ECG waveform 174 is displayed in accordance with surface signals received from the patient via the plurality of ECG leads 172 in a manner well understood by one of ordinary skill in the art. In the embodiment illustrated in FIG. 3, the ECG leads 156 provide signals to the ECG circuit 170 of the system 200. In various embodiments, the system 200 then displays the ECG waveform 174 in a variety of known formats, such as a Lead I, Lead II, or Lead III configuration via the display 134. The input devices 136 also provide the capability for a user to select among the various lead configurations available.

Another function that is provided, in certain embodiments, by the input devices 136 includes access to an automatic physician follow-up diagnostic to verify/monitor device 10 operation, patient condition, records of past anomalous cardiac events, records of therapy provided, implantable device battery charge state, etc. In certain embodiments, the system 200 can also provide emergency ventricular inhibited pacing (VVI) and/or fibrillation shock activation via the input devices 136. The input devices 136 can also provide up-down scrolling through available functions or operations as well as selection of available functions.

Figure 4:
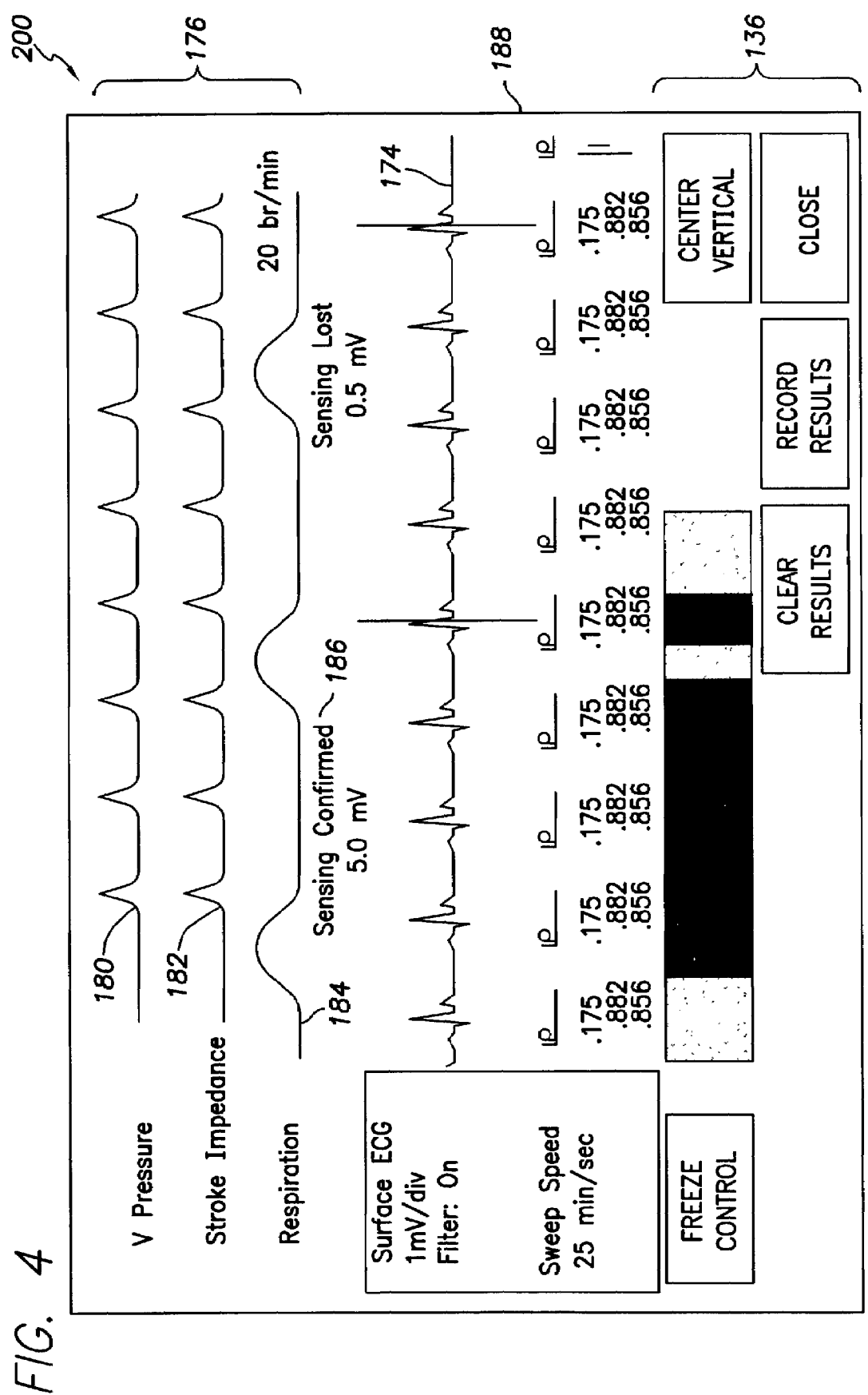
FIG. 4 is a screen shot of one embodiment of a display of the programmer of FIG. 3 with waveforms showing ventricular pressure, stroke impedance, respiration, and a surface ECG as well as marker data.

FIG. 4 illustrates one embodiment of functions and information that can be displayed on the display 134. However, it is to be understood that a variety of additional functions and data can be provided and made available via the input devices 136 and the display 134 in various other embodiments of the system 200 without detracting from the scope of the invention. It should also be understood that the functions and data made available via the display 134 and the input devices 136 can be programmable and that the functions and data used in a specific application may be a subset of a broader set available via the system 200.

The display 134 in the embodiment shown in FIG. 4 presents a surface ECG waveform 174 and a plurality of sensor waveforms 176 obtained from the at least one physiological sensor 108. In this embodiment, the sensor waveforms 176 include v pressure 180, stroke impedance 182, and respiration 184. The v pressure 180 and stroke impedance 182 waveforms provide hemodynamic information that is correlated with the electrical information provided by the surface ECG waveform 174. This cardiac information is also correlated with the respiratory information provided by the respiration waveform 184. This correlation and real-time presentation of a plurality of waveforms would enable a clinician to perform an extended study of the patient's condition and under different circumstances such as during treadmill exercise, medication dosing, etc. and reduce the need for other apparatus, such as a Holter monitor.

In this embodiment, the programmer 120 also displays descriptors 186 that indicate a confirmation of sensing at 5 mV and a loss of sensing at 8 mV. The programmer 120 also displays marker data 188 corresponding to each paced or sensed event.

As can be seen in FIG. 4, in certain embodiments, the system 200 can present data received from the at least one sensor 108 in a quasi-real-time or batched manner. In particular, the marker data 188 can include rate and interval/delay information that cannot readily be presented in a true real-time manner. For example, marker data 188 can include information such as an A-V delay and heart rate information that requires at least some calculation or processing in order to determine this information. Thus, there will generally be some delay in the presentation of certain information via the display 134 after the sensing of the sensor(s) 108. However, as previously mentioned, this quasi-real-time presentation is generally indistinguishable from true real-time presentation and for practical purposes is substantially identical.

It will also be understood, that in certain embodiments, the system 200 may batch or buffer information before presentation via the display 134. For example, the memory 94 of the device 10 may store a batch of data received from the sensor(s) 108 and periodically transmit this data as frames of data via the telemetry circuit 100. Alternatively or in combination, the memory and storage 126, 130, and 132 of the programmer 120 may buffer a batch of data received from the device 10 and present the data in frames via the display 134 and/or provide the data to other devices via the printer 150, CD-ROM 152 and/or floppy 154 drives, and/or parallel 156 and serial 160 ports. Buffering of data received from the device 10 can also provide the system 200 a brief period of time to correlate the data prior to presentation. Thus, for example the surface ECG waveform 174, plurality of sensor waveforms 176, descriptors 186, and marker data 188 provided as shown in FIG. 4 can either be presented in a quasi-real-time substantially continuous scrolling manner or in a screen refresh manner where the data is refreshed periodically as the system 200 accumulates a subsequent screen's worth of new data.

The programmer 120 also provides a plurality of control options via the input devices 136. The control options illustrated in FIG. 4 include a freeze control to enable a user to freeze the real-time display, such as to consider a particular frame of the data. The programmer 120 also provides the capability to store or clear a set of results as well as to scroll forwards and backwards through the results. It will be appreciated that the capability to store a real-time display frame enables a user to consider a frame of interest at a later time. The stored frame(s) can also be uploaded to other systems via at least one of the parallel IO 156 and the serial IO 160 ports and/or stored to a removable storage media such as provided by the CD-ROM drive 152 or the floppy drive 154.

Figure 5:
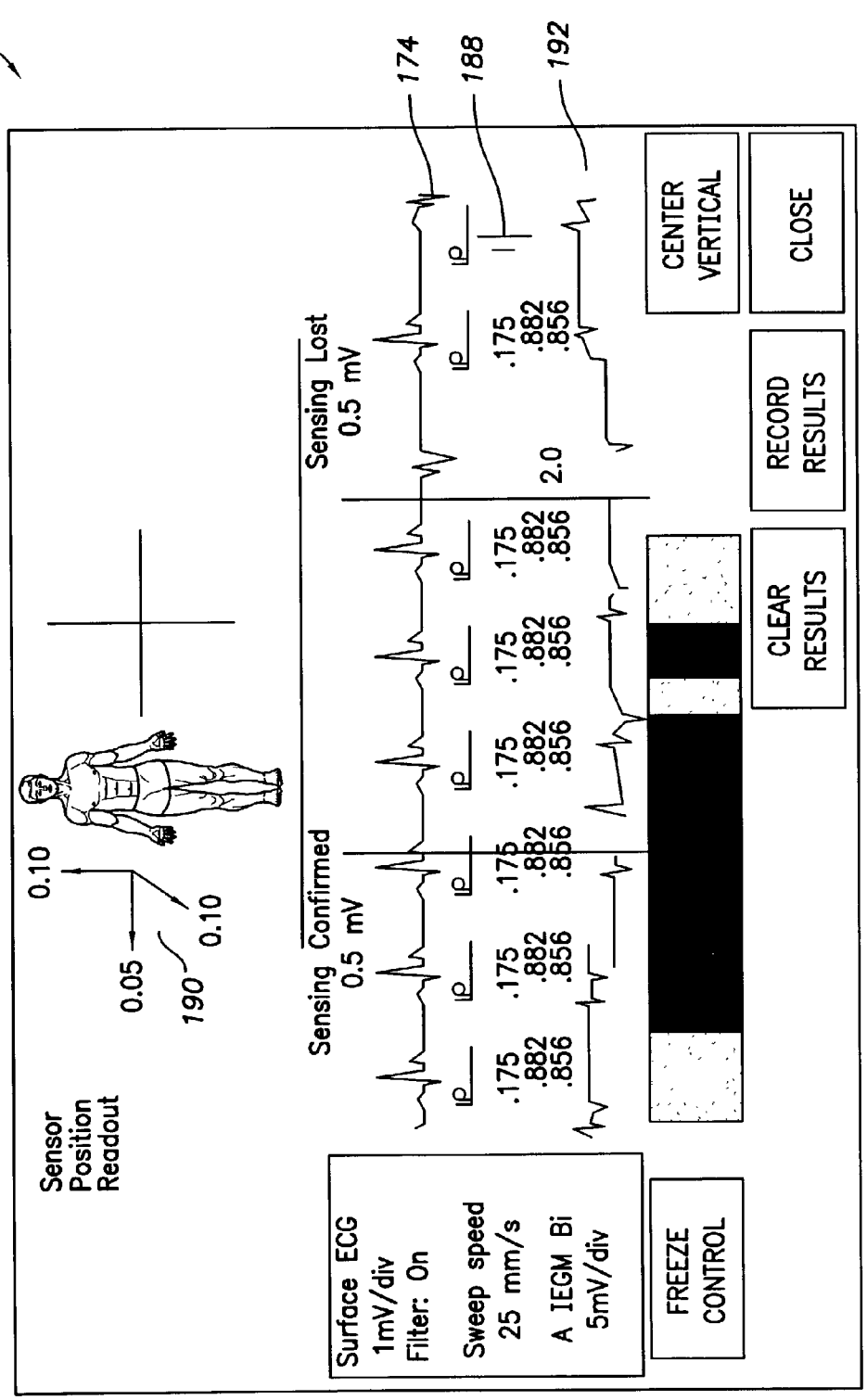
FIG. 5 is a screen shot of another embodiment of a display of the programmer of FIG. 3 with waveforms showing surface ECG correlated with an IEGM signal and a positional indicator of patient orientation as sitting with average three-axes acceleration.

FIG. 5 shows an embodiment wherein the programmer 120 displays the surface ECG waveform 174 and marker data 188 as well as a position signal 190 and an IEGM waveform 192. In this embodiment, the position signal 190 is obtained from a 3-d position sensor 108. The signal obtained from sensor 108 is processed to obtain a three-axis acceleration summary, which, in the illustrated embodiment, shows a 0.1 g vertical acceleration and a 0.05 g and a 0.10 g accelerations along perpendicular, horizontal axes. The position signal 190 also includes a graphic illustration of patient orientation, which in this embodiment, indicates a seated position.

The embodiment illustrated in FIG. 5 would be particularly useful in quantitatively evaluating a patient experiencing orthostatic hypertension. A clinician could extract quantitative information correlating the accelerations experienced by a patient as provided by the position waveform 190 in sitting upright from a prone position and/or standing from a prone or sitting position with cardiac information as provided by the surface ECG 174 and the IEGM 192 waveforms. This information is available on either a real-time basis or as stored data relating to past occurrences via the system 200.

Figure 6:
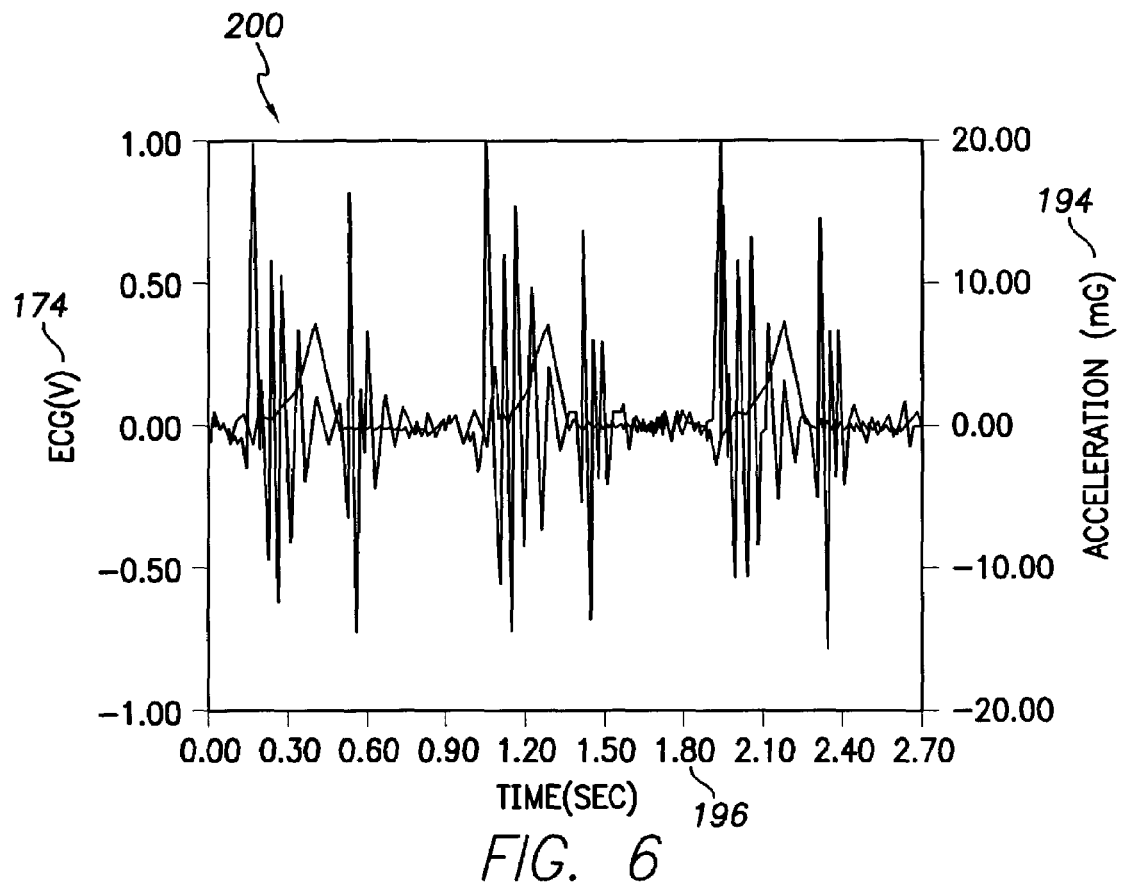
FIG. 6 is a screen shot of yet another embodiment of a display of the programmer of FIG. 3 with waveforms showing an ECG correlated with output of an accelerometer along a time-scale.
Figure 7:
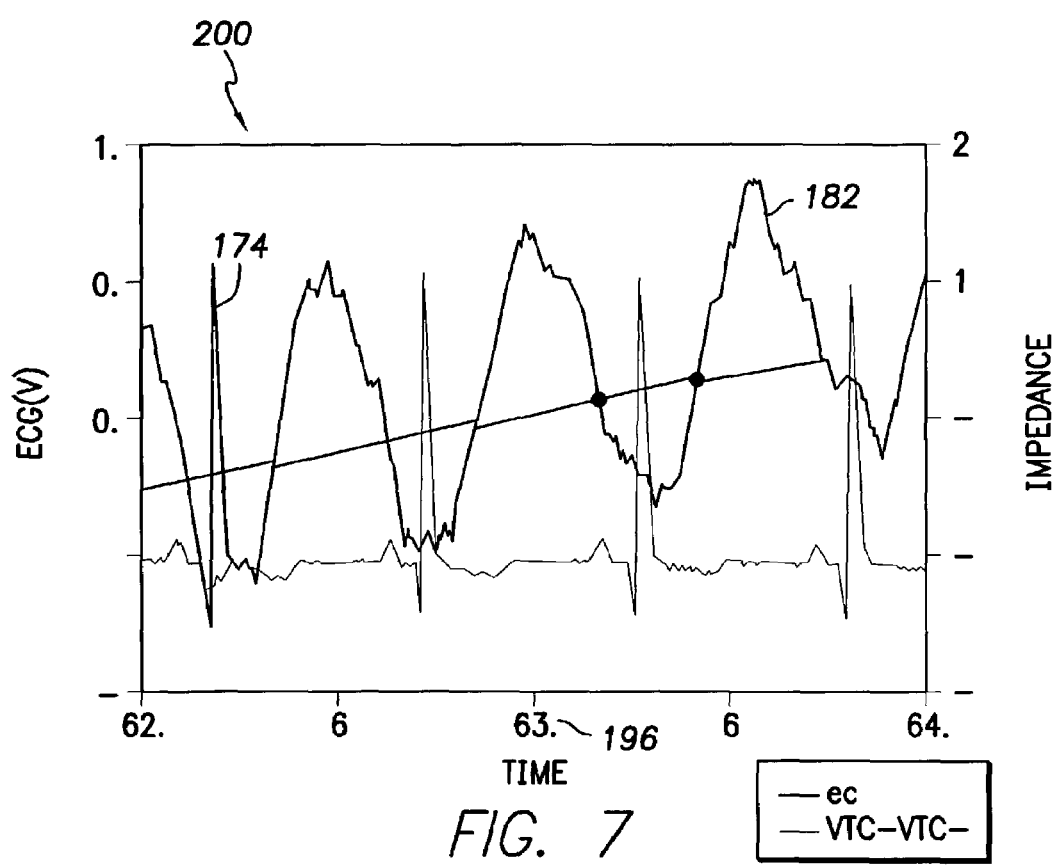
FIG. 7 is a screen shot of a further embodiment of a display of the programmer of FIG. 3 with cardiac or transthoracic impedance and surface ECG waveforms along a time-scale.

FIG. 6 shows another embodiment, wherein the programmer 120 displays correlated surface ECG waveform 174 with an instantaneous acceleration signal 194 along a time-scale 196. FIG. 7 shows yet another embodiment, wherein the programmer 120 displays a correlated surface ECG 174 and impedance 182 waveforms correlated with a time-scale 196. These embodiments offer the advantage of simultaneously overlaid waveforms providing different information along with a time-scale to provide ready reference to the duration and time spacing of the occurrences represented by the waveforms.

Figure 8:
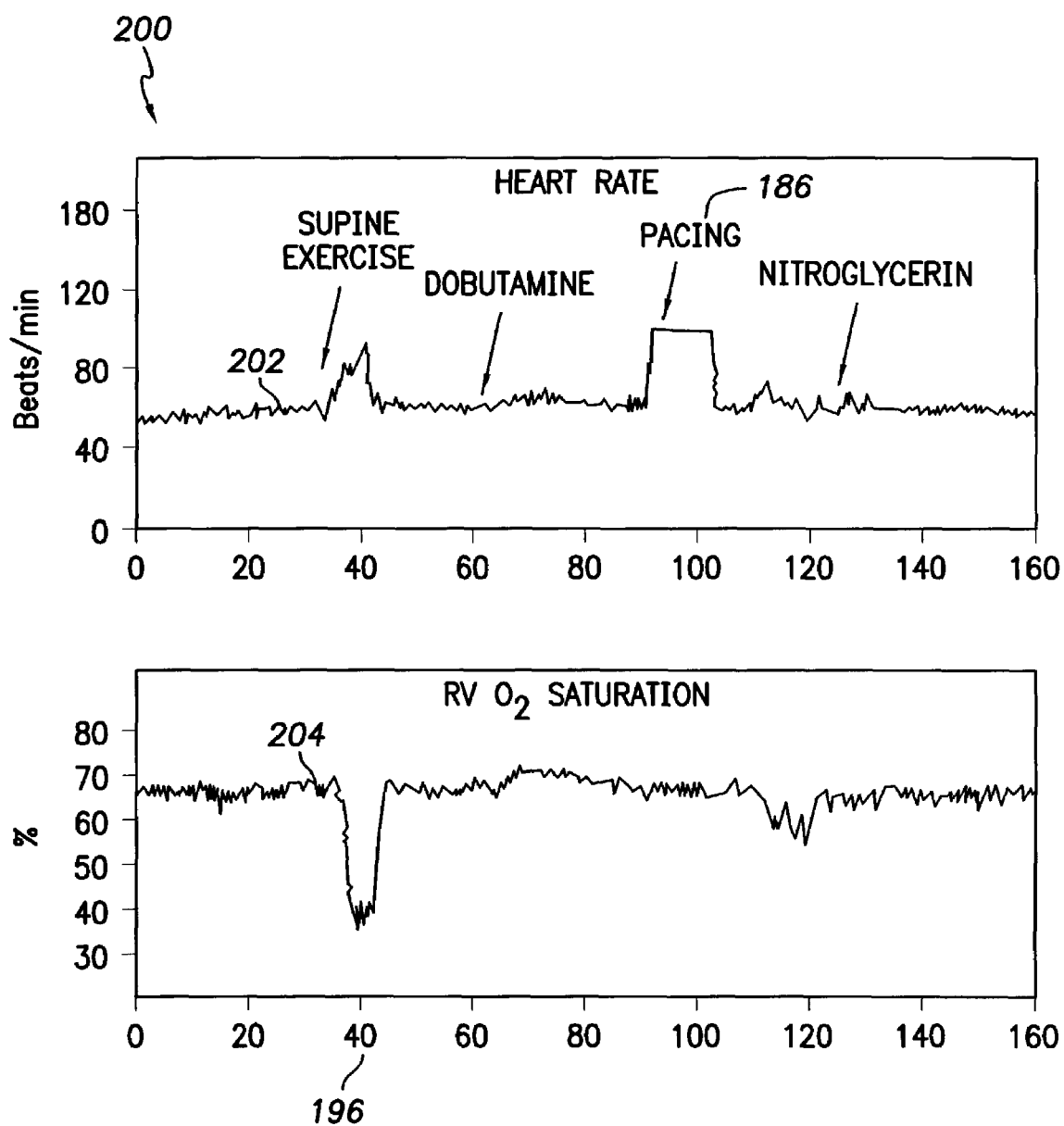
FIG. 8 is a screen shot of an additional embodiment of a display of the programmer of FIG. 3 with waveforms showing heart rate correlated with RV $O_2$ saturation with indicators indicating patient condition including supine exercise, Dobutamine and Nitroglycerin dosing, and pacing along a time-scale.

FIG. 8 shows a further embodiment, wherein the programmer 120 displays a derived waveform from the IEGM waveform 186, which in this embodiment comprises a rate waveform 202 showing a running average of heart rate in bpm as well as a directly measured RV $O_2$ saturation waveform 204 correlated along a time-scale 196. The programmer 120 in this embodiment also displays descriptors 186 of other patient information which in this illustration include periods of supine exercise, dosing with Dobutamine and Nitroglycerine, as well as a period of pacing along a time-scale.

It will be appreciated that the real-time or quasi-real-time concurrent display of multiple internally monitored physiological parameters as provided by implantable devices to a programmer provides a clinician with valuable diagnostic information at increased convenience to both the patient and attending staff. This reduces the need for other apparatus, such as Holter or other secondary monitors heretofore used. The multiple physiological parameters can include cardiac electrical activity, hemodynamic status, metabolic need, and patient orientation thus allowing a clinician to correlate the real-time waveforms provided by the system 200 with direct observation of the patient as well as optionally with other diagnostic tools. The system 200 also provides the capability to record frames of data for later retrieval that previously required additional instrumentation in addition to the implantable device.

Although the preferred embodiments of the present invention have shown, described and pointed out the fundamental novel features of the invention as applied to those embodiments, it will be understood that various omissions, substitutions and changes in the form of the detail of the device illustrated may be made by those skilled in the art without departing from the spirit of the present invention. Consequently, the scope of the invention should not be limited to the foregoing description but is to be defined by the appended claims.

What is claimed is:

1. A system comprising:
   an implantable cardiac stimulation device that is operative to internally monitor signals indicative of cardiac activity;
   at least one implantable sensor capable of monitoring at least one internally measured parameter, the at least one implantable sensor being detached from the implantable cardiac stimulation device;
   a programmer capable of providing control signals to the implantable cardiac stimulation device and of displaying information received from the implantable cardiac stimulation device and the at least one implantable sensor simultaneously so as to allow a clinician to simultaneously view the information in at least a quasi-real-time manner; and
   a telemetry system operative to establish a telemetry link between the programmer and the implantable cardiac stimulation device and the at least one implantable sensor, the telemetry system operative to establish a telemetry link directly between the implantable cardiac stimulation device and the at least one implantable sensor.

2. The system of claim 1, wherein the information received from the at least one implantable sensor and displayed on the programmer comprises pressure information.

3. The system of claim 2, wherein the pressure information comprises ventricular pressure data.

4. The system of claim 1, further comprising a surface monitor in communication with the programmer and providing surface signals indicative of patient status for display on the programmer.

5. The system of claim 4, wherein the surface signals comprise surface ECG signals.

6. The system of claim 4, wherein the surface monitor is in telemetric communication with the programmer.

7. The system of claim 1, wherein in a quasi-real-time manner comprises the implantable device providing data from at least one of the monitored parameters indicative of cardiac function and the implantable sensor in frames to the programmer.

8. The system of claim 1, wherein in a quasi-real-time manner comprises wherein the implantable device processes the information received from at least one of the implantable device and sensor and provides the programmer a signal derived from the processing.

9. The system of claim 8, wherein the processing comprises determining a rate.

10. The system of claim 1, wherein the data received from the implantable cardiac stimulation device is IEGM data.

11. A system comprising:
    an implantable medical device adapted to provide therapy to an organ of a patient, the implantable medical device monitoring at least a first parameter affecting delivery of therapy to the patient;
    an internal sensor that is operative to provide at least a second internally detected parameter affecting the delivery of therapy to the patient, the internal sensor being detached from the implantable medical device;
    an external programmer having a display and a user interface, wherein the external programmer is in communication with the implantable medical device and the internal sensor such that a medical professional can use the user interface to select among the parameters detected by the implantable medical device and internal sensor to produce one or more correlated real-time visual images on the display of the plurality of internally detected parameters to thereby allow the medical professional to simultaneously evaluate and compare the plurality of parameters; and
    a wireless communication system to provide direct wireless communication between the implantable medical device and the internal sensor.

12. The system of claim 11, further comprising an external sensor monitoring at least one physiological parameter of the patient corresponding to the at least first parameter such that the at least one physiological parameter detected by the implantable medical device can be simultaneously displayed with the corresponding physiological parameter detected by the external sensor to permit assessment of the performance of the implantable medical device in detecting the physiological parameter.

13. The system of claim 11, wherein the implantable device monitors a plurality of internal physiological parameters.

14. The system of claim 11, wherein the internal sensor monitors a plurality of internal physiological parameters.

15. The system of claim 11, wherein the physiological parameters include at least two of cardiac electrical activity, respiration, patient orientation, and hemodynamic status.

16. The system of claim 15, wherein hemodynamic status parameters comprise at least one of pressure and stroke volume.

17. A method comprising:
    providing an implantable cardiac stimulation device;
    sensing at least one parameter with the implantable cardiac stimulation device;
    sensing at least one parameter with the implantable sensor;
    wirelessly communicating between the implantable cardiac stimulation device and the implantable sensor;
    telemetrically transmitting the parameters sensed by each of the implantable cardiac stimulation device and the implantable sensor in at least quasi-real-time; and
    simultaneously displaying the parameters from each of the implantable device and the sensor via the display device in a correlated manner.

18. The method of claim 17, wherein in a correlated manner comprises time synchronized.

19. The method of claim 17, further comprising processing at least one of the parameters from the implantable device and the sensor and displaying the at least one parameter as derived data.

20. The method of claim 19, wherein the derived data comprises marker data.

21. The method of claim 17, further comprising displaying IEGM data derived from the implantable cardiac stimulation device.

* * * * *